United States Patent
Kim et al.

(10) Patent No.: US 11,427,547 B2
(45) Date of Patent: Aug. 30, 2022

(54) EDARAVONE PRODRUG COMPOUND AND PHARMACEUTICAL USE THEREOF IN TREATMENT OR ALLEVIATION OF NEURODEGENERATIVE OR MOTOR NEURON DISEASE

(71) Applicants: J2H BIOTECH INC., Suwon-Si (KR); THERAGEN ETEX CO., LTD, Ansan-Si (KR)

(72) Inventors: Jae-Sun Kim, Suwon-si (KR); Hyung-Chul Ryu, Osan-Si (KR); Jee-Woong Lim, Seongnam-Si (KR); Eun-Bi Kang, Pyeongtaek-Si (KR); Hyuk-Min Kim, Daejeon (KR); Hyunjun Yang, Anyang-Si (KR); Dukho Chang, Suwon-Si (KR); Dong-Gyu Kim, Suwon-Si (KR); Byung Hwan Ryoo, Seongnam-Si (KR); Yong-Ho Oh, Seoul (KR)

(73) Assignee: J2H BIOTECH INC., Suwon-si (KR)

( * ) Notice: Subject to any disclaimer, the term of this patent is extended or adjusted under 35 U.S.C. 154(b) by 0 days.

(21) Appl. No.: 17/276,351

(22) PCT Filed: Sep. 9, 2019

(86) PCT No.: PCT/KR2019/011639
§ 371 (c)(1),
(2) Date: Mar. 15, 2021

(87) PCT Pub. No.: WO2020/060092
PCT Pub. Date: Mar. 26, 2020

(65) Prior Publication Data
US 2022/0033359 A1 Feb. 3, 2022

(30) Foreign Application Priority Data
Sep. 17, 2018 (KR) .................... 10-2018-0111079

(51) Int. Cl.
*C07D 231/22* (2006.01)

(52) U.S. Cl.
CPC .................. *C07D 231/22* (2013.01)

(58) Field of Classification Search
CPC ..................................... C07D 231/22
See application file for complete search history.

(56) References Cited

U.S. PATENT DOCUMENTS

| 7,211,596 B2 | 5/2007 | Yoshida et al. |
| 2015/0080364 A1 | 3/2015 | Cisar et al. |

FOREIGN PATENT DOCUMENTS

| CN | 104098512 A | 10/2014 |
| CN | 102190622 B | 1/2015 |
| WO | 02-092082 A1 | 11/2002 |
| WO | 2018-133621 A1 | 7/2018 |

OTHER PUBLICATIONS

Huntington's disease overview [online] retrieved from the internet on Jan. 28, 2022 URL; https://mayoclinic.org/diseases-conditions/huntingtons-disease/symptoms-causes.*
Huntington's disease diagnosis [online] retrieved from the internet on Jan. 28, 2022 URL; https://mayoclinic.org/diseases-conditions/huntingtons-disease/diagnosis-treatment.*
International Search Report dated Dec. 30, 2019 for International Patent Application No. PCT/KR2019/011639, 4 pages with English translation.
Jiao et al., "Edaravone alleviates Alzheimer's disease-type pathologies and cognitive deficits", PNAS, 2015, vol. 112, No. 16, pp. 5225-5230.

* cited by examiner

*Primary Examiner* — Shawquia Jackson
(74) *Attorney, Agent, or Firm* — MH2 Technology Law Group, LLP

(57) ABSTRACT

The present invention provides a novel prodrug of an edaravone compound or a pharmaceutically acceptable salt thereof, a pharmaceutical composition comprising same as an active ingredient, and a use thereof in treatment or alleviation of neurodegenerative and/or motor neuron disease.

6 Claims, 1 Drawing Sheet

[Figure 1]
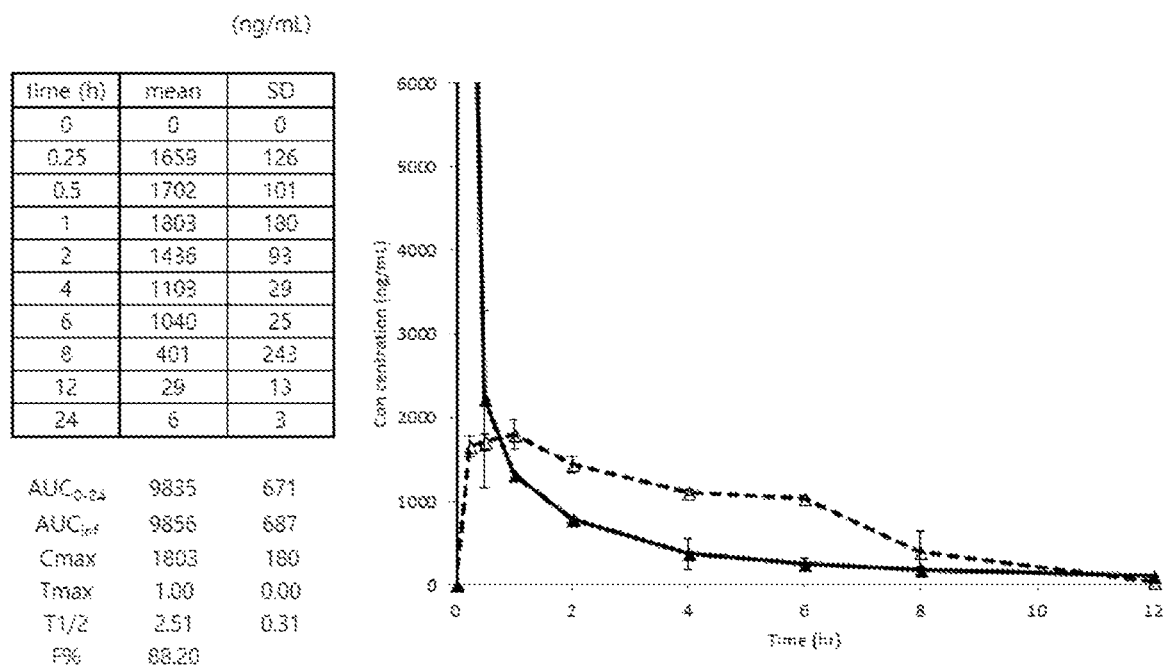
[Figure 2]
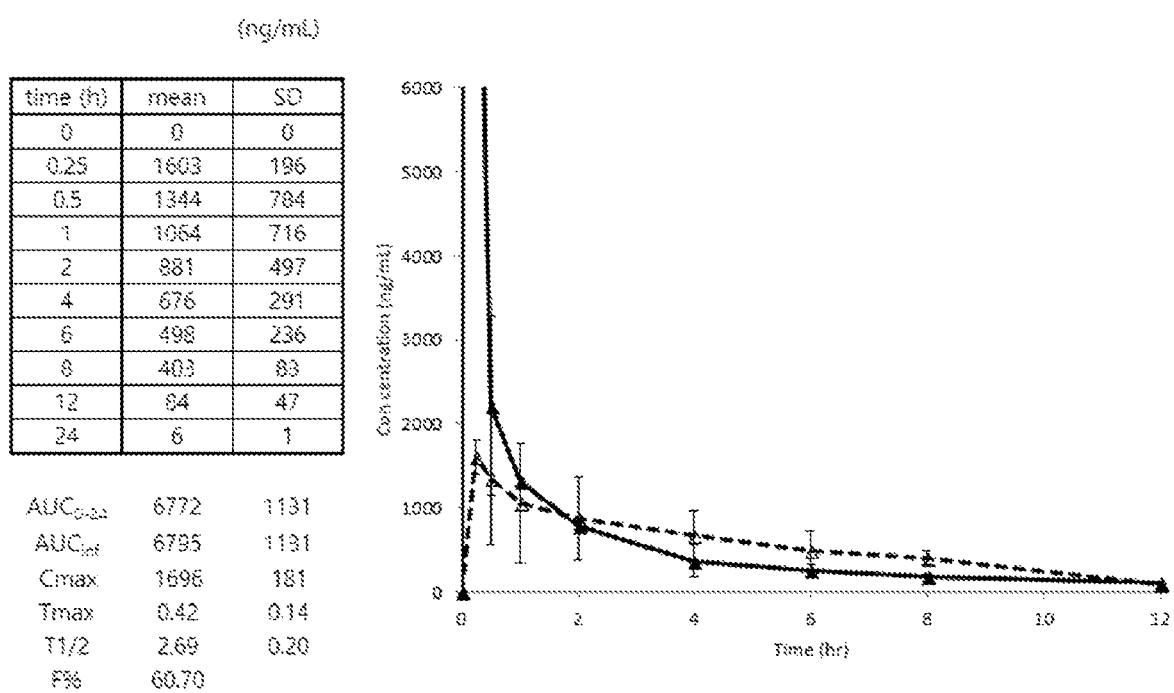

EDARAVONE PRODRUG COMPOUND AND PHARMACEUTICAL USE THEREOF IN TREATMENT OR ALLEVIATION OF NEURODEGENERATIVE OR MOTOR NEURON DISEASE

CROSS-REFERENCE TO RELATED APPLICATIONS

This application is a U.S. National Stage application of PCT/KR2019/011639 filed 9 Sep. 2019, which claims priority to Korean Patent Application No. 10-2018-0111079 filed 17 Sep. 2018, the entire disclosures of which are hereby incorporated by reference in their entireties.

TECHNICAL FIELD

The present invention relates to a novel prodrug of edaravone which is known to be useful in the treatment or improvement of neurodegenerative and motor neuron diseases such as Lou Gehrig's disease, or a pharmaceutically acceptable salt thereof. The present invention also relates to a pharmaceutical composition comprising such a novel prodrug or a pharmaceutically acceptable salt thereof as an active ingredient. The present invention also relates to a medical use using such a prodrug or a pharmaceutically acceptable salt thereof.

BACKGROUND ART

Currently, clinically used therapeutic agents for degenerative brain diseases or motor neuron disorders including Alzheimer's disease, Parkinson's disease, Huntington's disease, Lou Gehrig's disease (Amyotrophic lateral sclerosis), or multiple sclerosis as a representative disease are extremely limited. Various approaches have been taken for each disease to treat these diseases or to improve symptoms, and a mechanism that can be commonly applied to the treatment of this disease group is a method of inhibiting oxidative damage to nerve cells caused by the causative protein. That is, excessive production of radical oxygen species (ROS) leads to neurotoxicity, and antioxidants are used to reduce nerve degeneration by reducing nerve oxidative damage.

On the other hand, edaravone is a drug that was newly approved as a treatment for Lou Gehrig's disease in the United States in 2017, and its effect has been proven, such as improving the revised ALS functional rating scale (ALSFRS-R) in clinical trials and dramatically reducing the level of 3-nitrotyrosine in cerebrospinal fluid (CSF). (Expert Opinion on Pharmacotherapy, 2017, 18 (7), 735) Although the mechanism of action of edaravone on Lou Gehrig's disease has not been accurately identified, it is presumed that the antioxidant function of edaravone is a mechanism showing the therapeutic effect of Lou Gehrig's disease when considering the hypothesis of neuronal cell death due to oxidative stress related to ALS. It is presumed to be a mechanism showing the therapeutic effect of this ALS. (Frontiers in Aging Neuroscience, 2017, 9, 68)

On the other hand, Alzheimer's disease shows the accumulation of amyloid-O and pathological characteristics resulting therefrom. Edaravone is reported to inhibit the deposition of amyloid-beta and thereby oxidative damage and inhibit disease progression. (Proceedings of the National Academy of Sciences of the United States of America, 2015, 112 (16), 5225) That is, when edaravone was administered intraperitoneally in an animal model test using Alzheimer's disease-induced APPswe/PS1 mice, the behavioral improvement effect was demonstrated with reduction of amyloid-beta deposition and tau protein phosphorylation, and reduction of nerve inflammation and neuron loss.

In addition, Parkinson's disease shows a lack of dopamine substances in the basal ganglia, which is the motor nerve center. When edaravone was administered to a chronic rotenone rat model, a chronic Parkinson disease-induced animal, a muscle stiffness phenomenon (catalepsy), the regression of dopamine neurons and so on have been greatly improved. This was proven to be a result of the remarkable reduction of the oxygen species occurring in the midbrain by edaravone. (PLoS One, 2011, 6 (6), e20677)

Edaravone is currently commercialized as an intravenous infusion (IV infusion), and is generally administered to patients at a repeat cycle of 60 mg each time on a 28-day basis. In other words, after the initial administration for 14 days, it goes through a 14-day rest period, and then again edaravone was administered for 10 days out of 14 days, and then it goes through a 14-day rest period. However, from the patient's point of view, it is a very cumbersome process to visit the hospital for each administration and receive an injection for an hour. In particular, considering the movement of patients with reduced mobility due to the characteristics of Lou Gehrig's disease, administration of injections, and frequent administration schedules, it is extremely inadequate in terms of patient convenience despite the clinical usefulness of the drug.

Such discomfort may be solved by, for example, changing an IV infusion into an injection or further developing an oral formulation. However, edaravone has low solubility (1.85 mg/ml), low oral absorption rate ($F_{abs}$=5.23%), low permeability ($P_{eff}$=3.18×10$^{-7}$ cm/s), instability, excessive secondary metabolism (phase II metabolism: glucuronidation), and thus it is difficult to use the drug as an oral medication. In particular, the phenomenon that edaravone is released by P-glycoprotein (Pgp) present in intestinal epithelial cells is pointed out as a major cause.

On the other hand, Chinese Patent Publication No. 102190622 proposes prodrugs having a specific structure, which is a piperazine derivative linked to the edaravone structure with a carbamate functional group. These compounds were administered orally or injected into an animal model to measure their antioxidant effect. However, the above publication does not disclose the pharmacokinetic aspects of the in vivo administration of the compounds, and the publication also does not disclose or hint the blood concentration of edaravone generated from the prodrug.

As a result of the inventors' direct experimentation, the prodrugs disclosed in the Chinese patent were much insufficient to improve the bioavailability of edaravone, and therefore, the present inventors determined that a drug with more remarkably improved absorption and bioavailability was needed.

DISCLOSURE

Technical Problem

Therefore, the problem to be solved by the present invention is to provide a prodrug of edaravone with improved absorption rate, bioavailability, etc., a pharmaceutical composition comprising such a prodrug, and a medical use of such a prodrug for treating or improving neurodegenerative and/or motor neuron diseases.

Technical Solution

In order to solve the above problem, the present disclosure provides a compound represented by the following Chemical Formula 1 or a pharmaceutically acceptable salt thereof.

[Chemical Formula 1]

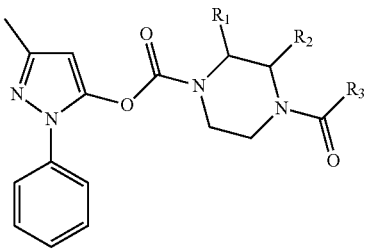

In the Chemical Formula 1, $R_1$ and $R_2$ are each independently hydrogen or ($C_1$-$C_3$) alkyl, $R_3$ is any one selected from the group consisting of ($C_1$-$C_3$)alkyl, ($C_3$-$C_7$)cycloalkyl, phenyl, —$CH_2NH_2$, —CH($CH_3$)$NH_2$, —CH($CH_2OH$)$NH_2$, —CH(CH($CH_3$)OH)$NH_2$, —CH($CH_2SH$)$NH_2$, —CH(CH($CH_3$)$_2$)$NH_2$, —CH(C($CH_3$)$_3$)$NH_2$, —CH($CH_2$CH($CH_3$)$_2$)$NH_2$, —CH(CH($CH_3$)$CH_2CH_3$)$NH_2$, —CH($CH_2CH_2SCH_3$)$NH_2$, pyrrolidin-2-yl, —CH($CH_2Ph$)$NH_2$, —CH($CH_2PhOH$-p)$NH_2$, —CH(1H-indole-3-yl-$CH_2$)$NH_2$, —CH($CH_2CO_2H$)$NH_2$, —CH($CH_2CH_2CO_2H$)$NH_2$, —CH($CH_2CONH_2$)$NH_2$, —CH($CH_2CH_2CONH_2$)$NH_2$, —CH(1H-imidazol-4-yl-$CH_2$)$NH_2$, —$CH_2CH_2CH_2CH_2NH_2$, and —$CH_2CH_2CH_2NHC(NH)NH_2$.

As a result of preparing and evaluating various prodrugs, the present inventors confirmed a very excellent effect in terms of absorption rate and bioavailability of the compound or a pharmaceutically acceptable salt thereof, and in addition to such bioavailability aspects, the present inventors confirmed excellent physical properties or characteristics of the compound or a pharmaceutically acceptable salt thereof as a prodrug, thereby the present invention was completed.

In one embodiment of the present invention, preferably, the compounds are 3-methyl-1-phenyl-1H-pyrazol-5-yl 4-acetylpiperazine-1-carboxylate;

(S)-3-methyl-1-phenyl-1H-pyrazol-5-yl 4-acetyl-2-methylpiperazine-1-carboxylate;

(R)-3-methyl-1-phenyl-1H-pyrazol-5-yl 4-acetyl-2-methylpiperazine-1-carboxylate;

3-methyl-1-phenyl-1H-pyrazol-5-yl 4-(cyclohexanecarbonyl)piperazine-1-carboxylate;

3-methyl-1-phenyl-1H-pyrazol-5-yl 4-benzoylpiperazine-1-carboxylate;

3-methyl-1-phenyl-1H-pyrazol-5-yl 4-(2-aminoacetyl)piperazine-1-carboxylate;

(S)-3-methyl-1-phenyl-1H-pyrazol-5-yl 4-(2-aminopropanoyl)piperazine-1-carboxylate;

(S)-3-methyl-1-phenyl-1H-pyrazol-5-yl 4-(2-amino-3-hydroxypropanoyl)piperazine-1-carboxylate;

(R)-3-methyl-1-phenyl-1H-pyrazol-5-yl 4-(2-amino-3-mercaptopropanoyl)piperazine-1-carboxylate;

(S)-3-methyl-1-phenyl-1H-pyrazol-5-yl 4-(2-amino-3-methylbutanoyl)piperazine-1-carboxylate;

(R)-3-methyl-1-phenyl-1H-pyrazol-5-yl 4-((S)-2-amino-3-methylbutanoyl)-2-methylpiperazine-1-carboxylate;

(S)-3-methyl-1-phenyl-1H-pyrazol-5-yl 4-((S)-2-amino-3-methylbutanoyl)-2-methylpiperazine-1-carboxylate;

(R)-3-methyl-1-phenyl-1H-pyrazol-5-yl 4-((S)-2-amino-3-methylbutanoyl)-2-ethylpiperazine-1-carboxylate;

(S)-3-methyl-1-phenyl-1H-pyrazol-5-yl 4-((S)-2-amino-3-methylbutanoyl)-3-methylpiperazine-1-carboxylate;

(S)-3-methyl-1-phenyl-1H-pyrazol-5-yl 4-(2-amino-3,3-dimethylbutanoyl)piperazine-1-carboxylate;

(S)-3-methyl-1-phenyl-1H-pyrazol-5-yl 4-(2-amino-4-(methylthio)butanoyl)piperazine-1-carboxylate;

(S)-3-methyl-1-phenyl-1H-pyrazol-5-yl 4-(2-amino-3-phenylpropanoyl)piperazine-1-carboxylate;

(S)-3-methyl-1-phenyl-1H-pyrazol-5-yl 4-(2,4-diamino-4-oxobutanoyl)piperazine-1-carboxylate;

or (S)-3-methyl-1-phenyl-1H-pyrazol-5-yl 4-(2,6-diaminohexanoyl)piperazine-1-carboxylate.

As used herein, if the term "$C_x$-$C_y$" is used, it means the number of carbon atoms is from x to y. For example, ($C_1$-$C_3$)alkyl means an alkyl which carbon number is any integer of from 1 to 3.

The term "alkyl" used in the present invention includes both linear and branched types.

As used herein, the term "pharmaceutically acceptable salt(s)" refers to a salt prepared from active compounds according to the present disclosure with relatively non-toxic acids or bases, depending on the particular substituents of those compounds. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Other examples of salts are disclosed in well-known literature on the art, for example, *Remington's Pharmaceutical Sciences*, 18$^{th}$ eds., Mack Publishing, Easton Pa. (1990) or *Remington: The Science and Practice of Pharmacy*, 19$^{th}$ eds, are disclosed in Mack Publishing, Easton Pa. (1995).

As used herein, the phrase "compound(s) of this/the invention" includes any compound(s) of Chemical Formula 1, as well as clathrates, hydrates, solvates, or polymorphs thereof. And, even if the term "compound(s) of the invention" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers. That is, if the compounds of Chemical Formula 1 according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

The compound represented by the Chemical Formula 1 of the present invention can be synthesized, for example, by the following route.

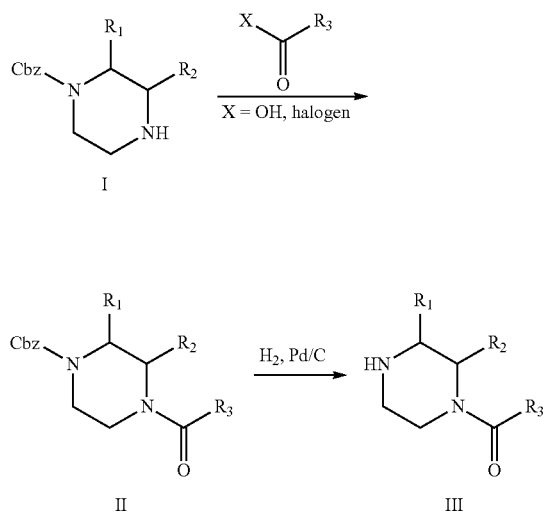

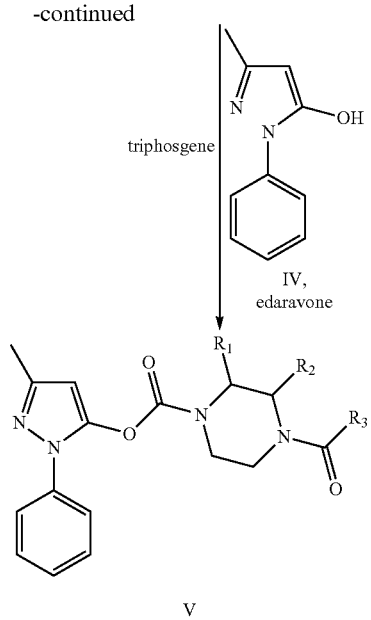

The first substance used is a piperazine compound I substituted with $R_1$ and $R_2$ consisting of an alkyl group, and an amide intermediate II can be obtained as a result of reaction with an activated ester compound or a carboxylic acid compound containing an $R_3$ group. The carboxylic acid compound used at this time may include an amino acid in which the amine group is properly protected, and the protecting group is t-butoxycarbonyl (Boc) or fluorenylmethyloxycarbonyl (Fmoc) which is commonly used in amine groups. As a next step, the group-protected carboxybenzyl (Cbz) group can be deprotected by hydrogenation to obtain intermediate III.

Intermediate III can be activated by treatment with triphosgene and then reacted with edaravone IV to obtain final compound V. Meanwhile, when an amino acid having an amine group protected is used, a deprotection process may be separately performed in the final step.

The present inventors have devised and manufactured a novel compound with a new structure capable of dramatically increasing the oral absorption rate upon oral administration by modifying the chemical structure of the edaravone compound. The blood concentration of the edaravone substance after in vivo oral administration of the novel compound is ultimately directly proportional to the efficacy of the drug for treating or improving various neurodegenerative and/or motor neuron diseases. This means that intravenous and oral doses can be proportionally applied by comparing the concentration of edaravone exposed in blood through a metabolic process after oral administration of the prodrug according to the present invention based on the blood concentration of edaravone after intravenous administration.

The present inventors prepared and evaluated compounds having various chemical structures in order to derive a novel compound with improved oral absorption. In addition, in terms of the physicochemical aspect of the compound, the absorption of the drug was evaluated by considering the degree of lipophilicity, taking into account that the absorption of the drug is basically performed by passive diffusion. In order to prevent a decrease of absorption due to an excessively low water solubility, it was also evaluated whether the minimum solubility could be exhibited.

Particularly, it is thought that some of the compounds according to the present invention can act as a substrate for amino acid transporters such as PepT1 and LAT1 among transmembrane transporters present in the intestinal membrane. Therefore, while edaravone has low bioavailability due to Pgp release, some of the compounds according to the present invention are considered to have a remarkably increased bioavailability due to active transport by an amino acid transporter. However, the present invention is not limited to this theoretical mechanism.

Specifically, for example, the pharmacokinetic evaluation result of the compound of Example 10 below among the compounds of Chemical Formula 1 showed 88.2% of bioavailability when administered orally compared to edaravone administered intravenously. It was also confirmed that its oral bioavailability increased by about 18 times compared to the bioavailability (4.9%) of edaravone administered orally. In addition, in the pharmacokinetic evaluation results for the compound of Example 15 below, the bioavailability of the compound of Example 15 administered orally was 60.7% compared to the edaravone administered intravenously, and it was a significant increase of 12 times compared to the bioavailability (4.9%) of edaravone administered orally.

Meanwhile, the pharmacokinetic property of the Example 2 compound of Chinese Patent CN 102190622, that is, 4-methyl-1-piperazinformyledaravone (same as the Reference Example 1 compound of this application; 3-methyl-1-phenyl-1H-pyrazol-5-yl 4-methylpiperazine-1-carboxylate) was evaluated and compared in the same manner as the example compounds newly presented in the present invention. As a result, the bioavailability of this compound was 12.0%. Therefore, the compounds of Chemical Formula 1 presented in the present invention, including the compounds of Examples 10 and 15 mentioned above, shows greatly improved oral bioavailability compared to the known substance of CN 102190622.

In another embodiment, the present invention provides a pharmaceutical composition comprising a therapeutically effective amount of the compound of Chemical Formula 1 or a pharmaceutically acceptable salt thereof according to the present invention, and a pharmaceutically acceptable carrier.

As used herein, an "effective amount" means an amount of a compound of the present invention slowing or minimizing neurodegenerative and/or motor neuron disease; or sufficient to provide a therapeutic benefit in the treatment or management of neurodegenerative and/or motor neuron disease.

As the pharmaceutically acceptable carrier, for example, a carrier for oral administration or a carrier for parenteral administration may be used. Carriers for oral administration may include lactose, starch, cellulose derivatives, magnesium stearate, stearic acid, and the like. In addition, carriers for parenteral administration may include water, suitable oil, saline, aqueous glucose and glycol, and the like, and may further include stabilizers and preservatives. Suitable stabilizers may be antioxidants such as sodium hydrogen sulfite, sodium sulfite or ascorbic acid. Suitable preservatives may be benzalkonium chloride, methyl- or propyl-paraben and chlorobutanol. Other pharmaceutically acceptable carriers may be referred to as those described in the following documents. (Remington's Pharmaceutical Sciences, 19th ed., Mack Publishing Company, Easton, Pa., 1995)

The pharmaceutical composition of the present invention can be administered to mammals including humans by any route of administration. It can be administered orally or parenterally. However, the oral route of administration is more preferable in terms of the fact that the compounds of the present invention show excellent oral absorption.

Parenteral administration methods include, for example, but are not limited thereto, intravenous, intramuscular, intraarterial, intramedullary, intrathecal, intracardiac, transdermal, subcutaneous, intraperitoneal, intranasal, intestinal, topical, sublingual or rectal administration. For example, the pharmaceutical composition of the present invention may be prepared in an injectable formulation and administered by a method of lightly pricking the skin with a 30 gauge thin injection needle, or directly applying it to the skin.

The pharmaceutical composition of the present invention may be formulated as a formulation for oral administration or parenteral administration according to the route of administration as described above.

In the case of a formulation for oral administration, the composition of the present invention may be formulated using a method known in the art such as powder, granule, tablet, pill, dragee, capsule, liquid, gel, syrup, slurry, suspension, etc. For example, oral preparations can be obtained as a tablet by blending the active ingredient with a solid excipient, pulverizing it, adding a suitable adjuvant, and processing it into a granule mixture. Examples of suitable excipients include sugars including as lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethyl-cellulose; gelatin; polyvinylpyrrolidone; and the like. In addition, in some cases, cross-linked polyvinylpyrrolidone, agar, alginic acid or sodium alginate may be added as a disintegrant. Furthermore, the pharmaceutical composition of the present invention may further comprise an anti-aggregating agent, a lubricant, a wetting agent, a flavoring agent, an emulsifying agent and a preservative.

In the case of a formulation for parenteral administration, it can be formulated in the form of injections, creams, lotions, ointments for external use, oils, moisturizers, gels, aerosols, and nasal inhalants by a method known in the art. These formulations are described in Remington's Pharmaceutical Science, 15th Edition, 1975. Mack Publishing Company, Easton, Pa. 18042, Chapter 87: Blaug, Seymour, which is well known for all pharmaceutical chemistry.

The total dosage of the pharmaceutical composition of the present invention may be administered to a patient as a single dose, and may be administered by a fractionated treatment protocol that is administered for a long time in multiple doses. The pharmaceutical composition of the present invention may vary the content of the active ingredient according to the symptoms of the disease. Preferably, the preferred total dose of the composition of the present invention may be about 0.01 µg to 1,000 mg, most preferably 0.1 µg to 100 mg per 1 kg of the patient's body weight per day. However, the appropriate effective dosage of the pharmaceutical composition of the present invention can be determined by conventional knowledge in the art based on the route of administration and the number of treatments as well as various factors such as the patient's age, weight, health condition, sex, disease severity, diet, and excretion rate. The pharmaceutical composition according to the present invention is not particularly limited to any specific formulation, route of administration, and method of administration as long as it exhibits the effects of the present invention.

In addition, the pharmaceutical composition of the present invention may be administered as an individual therapeutic agent or administered in combination with other therapeutic agents. When administered in combination with other therapeutic agents, the composition of the present invention and the other therapeutic agents may be administered simultaneously, individually or sequentially. At this time, the other therapeutic agent may be a substance already known to have an effect of treating or improving neurodegenerative and/or motor neuron diseases. When the pharmaceutical composition of the present invention is administered in combination with another therapeutic agent, the composition of the present invention and the other therapeutic agent may be separately formulated into separate containers, or may be formulated in combination in the same formulation.

In order to administer the compound presented in the present invention to the human body, a representative pharmaceutical method is described in detail by using a tablet as shown in Table 1 below. Compound A and Compound B presented below refer to substances presented as active ingredients for the treatment, improvement or prevention of neurodegenerative and motor neuron diseases in the present invention.

TABLE 1

| (Unit: mg per tablet) | Composition 1 | Composition 2 |
|---|---|---|
| Active ingredient | Compound A | Compound B |
|  | 30 | 60 |
| Lactose | 20 | 30 |
| Sodium lauryl sulfate (SLS) | 5 | 10 |
| Polyvinyl pyrrolidone (PVP) | 2 | 2 |
| Sodium croscarmellose | 5 | 5 |
| Microcrystalline cellulose | — | 10 |
| Magnesium stearate | 3 | 3 |
| Total weight | 65 | 120 |

The present invention also provides a pharmaceutical composition for the treatment or improvement of neurodegenerative or motor neuron diseases, comprising the compound of Chemical Formula 1 or a pharmaceutically acceptable salt thereof according to the present invention as an active ingredient. That is, the present invention provides a medical use of the compound of Chemical Formula 1 or a pharmaceutically acceptable salt thereof according to the present invention for the treatment or improvement of neurodegenerative or motor neuron diseases.

In another embodiment, the present invention provides a method for treating or ameliorating a neurodegenerative or motor neuron disease comprising administering a therapeutically effective amount of a compound of Chemical Formula 1 or a pharmaceutically acceptable salt thereof to a subject in need thereof. The neurodegenerative or motor neuron disease is Alzheimer's disease, Parkinson's disease, Huntington's disease, Lou Gehrig's disease, multiple sclerosis, dystonia, spinal muscular atrophy, inflammatory neuropathy, or alcoholic dementia. In another aspect, the subject is a human. In one embodiment, the treatment is preventative treatment. In another embodiment, the treatment is palliative treatment. In another embodiment, the treatment is restorative treatment.

Advantageous Effects

The present invention provides a compound effective in the treatment or amelioration of neurodegenerative or motor neuron diseases, a pharmaceutical composition comprising it as an active ingredient, their medical use, and a therapeutic method comprising administering it to a subject in need of treatment or prevention. The compound according to the present invention or a pharmaceutically acceptable salt thereof has various advantages as an active ingredient of a medical product in various aspects such as solubility, and particularly has excellent bioavailability after oral administration.

BRIEF DESCRIPTION OF DRAWINGS

FIG. 1 is a graph of the blood concentration of edaravone over time that appears after intravenous administration of a comparative compound, edaravone, and a single oral administration of a compound of Example 10, one embodiment according to the present invention. In FIG. 1, ▲ is the result of the edaravone intravenous administration group, and Δ is the result of the oral administration group of the Example 10 compound.

FIG. 2 is a graph of the blood concentration of edaravone over time that appears after intravenous administration of edaravone, a comparative compound, and a single oral administration of a compound of Example 15, another embodiment according to the present invention. In FIG. 2, ▲ is the result of the edaravone intravenous administration group, and Δ is the result of the oral administration group of the Example 15 compound.

MODE FOR INVENTION

The present invention will be described in more detail based on the following examples, but this is not intended to limit the scope of the present invention. In addition, those of ordinary skill in the art will be able to add various modifications and variations to the present invention within the scope not detrimental to the spirit of the present invention.

First, examples of the compound of Chemical Formula 1 according to the present invention are described below. Representative examples along with specific preparation steps are described below, and compounds having different substituents may be prepared through similar steps. Those of ordinary skill in the art will be able to easily prepare compounds of Chemical Formula 1 with different substituents with reference to the following representative examples.

Reference Example 1:
3-methyl-1-phenyl-1H-pyrazol-5-yl
4-methylpiperazine-1-carboxylate Hydrochloride

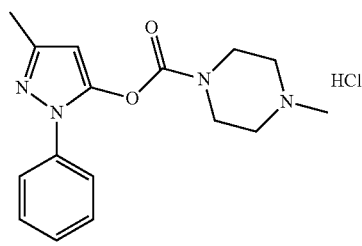

1.0 g of 1-methylpiperazine was dissolved in 10 ml of dichloromethane, and 1.2 ml of pyridine (1.5 eq.) was added. The reaction solution was cooled to 0° C. or less under an argon gas environment, and then 3.5 g (1.2 eq.) of triphosgene diluted in 15 ml of dichloromethane was slowly added thereto and stirred. After stirring at room temperature for 2 hours, it was washed with 25 ml of saturated brine, and the organic layer was separated. After drying over anhydrous magnesium sulfate, it was concentrated under reduced pressure to obtain a yellow oily substance. After completely dissolving by adding 10 ml of acetonitrile, 1.74 g (1.0 eq.) of edaravone and 9.76 g (3 eq.) of cesium carbonate were added thereto. After stirring at room temperature for 4 hours, the reaction solution was filtered using Celite, and the filtrate was recovered and concentrated under reduced pressure. The residue was dissolved with 25 ml of ethyl acetate, washed with 25 ml of saturated brine, and the organic layer was separated, dried over anhydrous magnesium sulfate, and concentrated under reduced pressure. 1.0 ml of concentrated hydrochloric acid solution and 10 ml of ethyl acetate were added to the concentrated residue, followed by concentration under reduced pressure. 10 ml of ethyl acetate was added thereto, and after concentration under reduced pressure, this process was repeated three times to crystallize to obtain 0.61 g of the title compound. (Yield 18.1%)

$^1$H NMR (400 MHz, DMSO-d6) δ 2.05 (s, 3H), 2.70 (s, 3H), 2.77-3.30 (m, 8H), 5.95 (s, 1H), 7.15-7.42 (m, 5H)

Synthesis Example 1

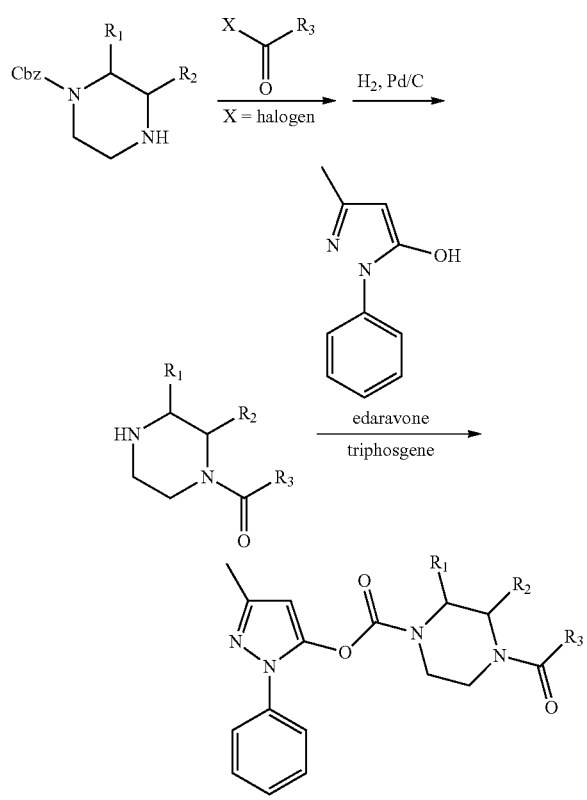

After dissolving the benzyl piperazine-1-carboxylate derivative in 10-fold volume of dichloromethane, 1.2 equivalents of triethylamine and 1.1 equivalents of the activated ester compound were added. The mixture was stirred for 2 hours at room temperature under an argon gas environment, washed with saturated brine, dried over anhydrous magnesium sulfate, and concentrated under reduced pressure. The residue was dissolved in tetrahydrofuran, 5% amount of palladium adsorbed on 10 wt % pure carbon was added thereto, followed by stirring at room temperature under hydrogen gas at atmospheric pressure. After the reaction was completed, the reaction solution was filtered, and the filtrate was recovered and concentrated under reduced pressure. It was purified by column chromatography using silica gel (eluent: a mixture of dichloromethane and methanol) to obtain an acylated piperazine intermediate. A 10-fold volume of dichloromethane was added thereto, dissolved, and 1.5 equivalents of pyridine were added. The reaction solution was cooled to 0° C. or less under an argon gas environment, and then 1.2 equivalents of triphosgene diluted in 15-fold volume of dichloromethane were slowly added dropwise and stirred. After stirring for 2 hours while maintaining 0-5° C., the mixture was washed with saturated brine and the organic layer was separated. After drying over anhydrous magnesium sulfate, it was concentrated under reduced pressure to obtain a yellow oily substance. After 10-fold volume of acetonitrile was added and completely dissolved, 1.0 equivalent of edaravone and 3.0 equivalent of cesium carbonate were added thereto. After stirring at room temperature to confirm the completion of the reaction, the reaction solution was filtered using Celite, and the filtrate was recovered and concentrated under reduced pressure. The residue was dissolved with 10-fold volume of ethyl acetate, washed with saturated brine, and the organic layer was separated, dried over anhydrous magnesium sulfate, and then concentrated under reduced pressure. The concentrated residue was purified by column chromatography using silica gel (eluent: a mixture of ethyl acetate and normal hexane) to obtain the target compound.

Synthesis Example 2

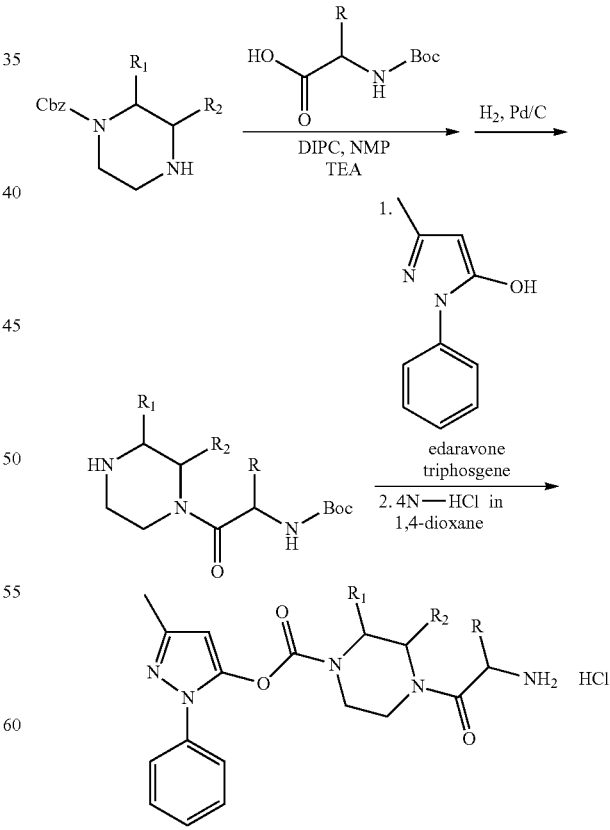

After dissolving the benzyl piperazine-1-carboxylate derivative in 5-fold volume of dichloromethane and 5-fold volume of N-methyl-2-pyrrolidone (NMP), 1.0 equivalent of amino acid in which the amine group was protected with t-butoxycarbonyl (Boc), 1.1 equivalent of diisopropylcarbodiimide (DIPC), and 1.2 equivalent of triethylamine were added. The mixture was stirred for 2 hours at room temperature under an argon gas environment, washed with saturated brine, dried over anhydrous magnesium sulfate, and concentrated under reduced pressure. The residue was dissolved in tetrahydrofuran, 5% amount of palladium adsorbed on 10 wt % pure carbon was added thereto, followed by stirring at room temperature under hydrogen gas at normal pressure. After the reaction was completed, the reaction solution was filtered, and the filtrate was recovered and concentrated under reduced pressure. It was purified by column chromatography using silica gel (eluent: a mixture of dichloromethane and methanol) to obtain an acylated piperazine intermediate. A 10-fold volume of dichloromethane was added thereto, dissolved, and 1.5 equivalents of pyridine were added. The reaction solution was cooled to 0° C. or less under an argon gas environment, and then 1.2 equivalents of triphosgene diluted in 15-fold volume of dichloromethane were slowly added dropwise and stirred. After stirring at room temperature for 2 hours, it was washed with saturated brine and the organic layer was separated. After drying over anhydrous magnesium sulfate, it was concentrated under reduced pressure to obtain a yellow oily substance. After 10-fold volume of acetonitrile was added thereto and completely dissolved, 1.0 equivalent of edaravone and 3.0 equivalent of cesium carbonate were added thereto. After stirring at room temperature to confirm the completion of the reaction, the reaction solution was filtered using Celite, and the filtrate was recovered and concentrated under reduced pressure. The residue was dissolved with 10-fold volume of ethyl acetate, washed with saturated brine, and the organic layer was separated, dried over anhydrous magnesium sulfate, and then concentrated under reduced pressure. The concentrated residue was purified by column chromatography using silica gel (eluent: a mixture of ethyl acetate and normal hexane). To the obtained intermediate, 5 equivalents of a 1,4-dioxane solution in which 4N-hydrochloric acid was dissolved was added to completely dissolve, and the mixture was stirred at room temperature for 30 minutes and concentrated under reduced pressure. After 10-fold volume of ethyl acetate was added thereto, it was concentrated under reduced pressure. (This was repeated 3 times) Finally, 10-fold volume of ethyl acetate was added, and the obtained suspension was filtered to obtain the target compound in a solid state.

Example 1: 3-Methyl-1-phenyl-1H-pyrazol-5-yl 4-acetylpiperazine-1-carboxylate

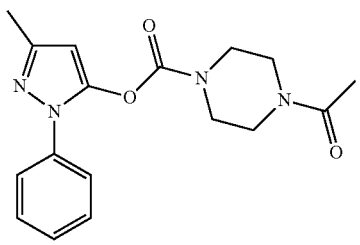 [SMILES: CC(=O)N1CCN(C(=O)Oc2cc(C)nn2-c2ccccc2)CC1]

Using 1.0 g of benzyl piperazine-1-carboxylate and 0.36 ml of acetyl chloride, 0.64 g (42.9%) of the title compound as a pale yellow solid was obtained according to the method of Synthesis Example 1. The results of nuclear magnetic resonance analysis and mass spectrometry are shown in Table 2 below.

Example 2: (S)-3-methyl-1-phenyl-1H-pyrazol-5-yl 4-acetyl-2-methylpiperazine-1-carboxylate

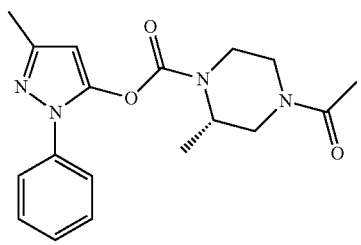 [SMILES: CC(=O)N1CCN(C(=O)Oc2cc(C)nn2-c2ccccc2)[C@@H](C)C1]

Using 1.0 g of (S)-benzyl 2-methylpiperazine-1-carboxylate and 0.34 ml of acetyl chloride, 0.60 g (41.1%) of the title compound as a pale yellow solid was obtained according to the method of Synthesis Example 1. The results of nuclear magnetic resonance analysis and mass spectrometry are shown in Table 2 below.

Example 3: (R)-3-methyl-1-phenyl-1H-pyrazol-5-yl 4-acetyl-2-methylpiperazine-1-carboxylate

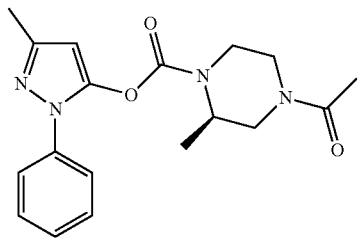 [SMILES: CC(=O)N1CCN(C(=O)Oc2cc(C)nn2-c2ccccc2)[C@H](C)C1]

Using 1.0 g of (R)-benzyl 2-methylpiperazine-1-carboxylate and 0.34 ml of acetyl chloride, 0.72 g (49.3%) of the title compound as a pale yellow solid was obtained according to the method of Synthesis Example 1. The results of nuclear magnetic resonance analysis and mass spectrometry are shown in Table 2 below.

Example 4: 3-Methyl-1-phenyl-1H-pyrazol-5-yl 4-(cyclohexanecarbonyl)piperazine-1-carboxylate

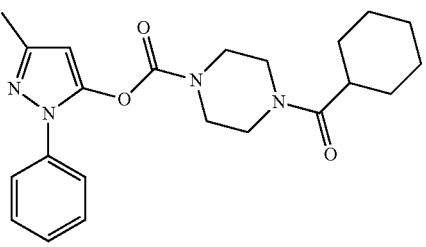 [SMILES: Cc1cc(OC(=O)N2CCN(C(=O)C3CCCCC3)CC2)n(-c2ccccc2)n1]

Using 1.0 g of benzyl piperazine-1-carboxylate and 0.67 ml of cyclohexanecarbonyl chloride, 0.41 g (22.8%) of the title compound as a pale yellow solid was obtained according to the method of Synthesis Example 1. The results of nuclear magnetic resonance analysis and mass spectrometry are shown in Table 2 below.

Example 5: 3-Methyl-1-phenyl-1H-pyrazol-5-yl 4-benzoylpiperazine-1-carboxylate

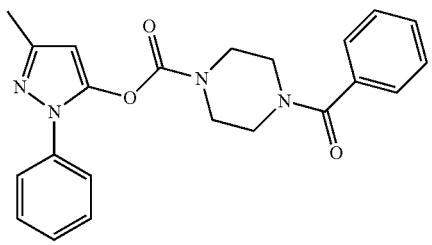 [SMILES: Cc1cc(OC(=O)N2CCN(C(=O)c3ccccc3)CC2)n(-c2ccccc2)n1]

Using 1.0 g of benzyl piperazine-1-carboxylate and 0.58 ml of benzoyl chloride, 0.84 g (47.4%) of the title compound as an off-white solid was obtained according to the method of Synthesis Example 1. The results of nuclear magnetic resonance analysis and mass spectrometry are shown in Table 2 below.

Example 6: 3-Methyl-1-phenyl-1H-pyrazol-5-yl 4-(2-aminoacetyl)piperazine-1-carboxylate Hydrochloride

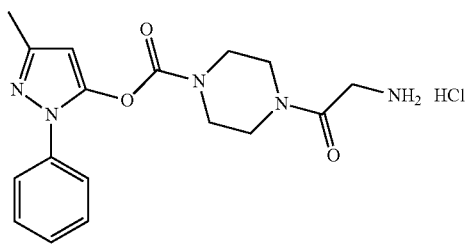 [SMILES: Cc1cc(OC(=O)N2CCN(C(=O)CN)CC2)n(-c2ccccc2)n1 ; Cl]

Using 1.0 g of benzyl piperazine-1-carboxylate and 0.80 g of N-Boc-glycine, 0.42 g (24.4%) of the title compound as an off-white solid was obtained according to the method of Synthesis Example 2. The results of nuclear magnetic resonance analysis and mass spectrometry are shown in Table 2 below.

Example 7: (S)-3-methyl-1-phenyl-1H-pyrazol-5-yl 4-(2-aminopropanoyl)piperazine-1-carboxylate Hydrochloride

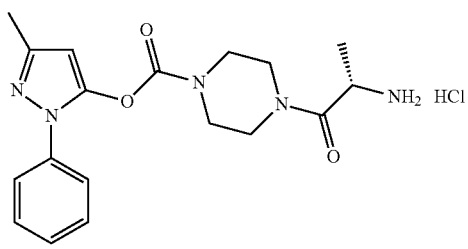 [SMILES: Cc1cc(OC(=O)N2CCN(C(=O)[C@H](C)N)CC2)n(-c2ccccc2)n1 ; Cl]

Using 1.0 g of benzyl piperazine-1-carboxylate and 0.86 g of N-Boc-alanine, 0.38 g (21.3%) of the title compound as an off-white solid was obtained according to the method of Synthesis Example 2. The results of nuclear magnetic resonance analysis and mass spectrometry are shown in Table 2 below.

Example 8: (S)-3-methyl-1-phenyl-1H-pyrazol-5-yl 4-(2-amino-3-hydroxypropanoyl)piperazine-1-carboxylate Hydrochloride

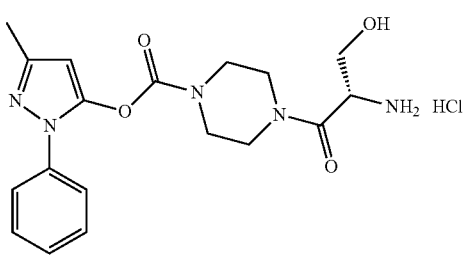 [SMILES: Cc1cc(OC(=O)N2CCN(C(=O)[C@@H](N)CO)CC2)n(-c2ccccc2)n1 ; Cl]

Using 1.0 g of benzyl piperazine-1-carboxylate and 1.45 g of N-Boc-O-TBS-serine, 0.29 g (15.6%) of the title compound as an off-white solid was obtained according to the method of Synthesis Example 2. The results of nuclear magnetic resonance analysis and mass spectrometry are shown in Table 2 below.

Example 9: (R)-3-methyl-1-phenyl-1H-pyrazol-5-yl 4-(2-amino-3-mercaptopropanoyl)piperazine-1-carboxylate Hydrochloride

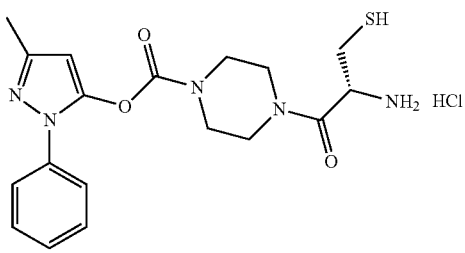 [SMILES: Cc1cc(OC(=O)N2CCN(C(=O)[C@@H](N)CS)CC2)n(-c2ccccc2)n1 ; Cl]

Using 1.0 g of benzyl piperazine-1-carboxylate and 1.71 g of N-Boc-S-triisopropylsilyl-cysteine, 0.18 g (9.3%) of the title compound as a pale yellow solid was obtained according to the method of Synthesis Example 2. The results of nuclear magnetic resonance analysis and mass spectrometry are shown in Table 2 below.

Example 10: (S)-3-methyl-1-phenyl-1H-pyrazol-5-yl 4-(2-amino-3-methylbutanoyl)piperazine-1-carboxylate Hydrochloride

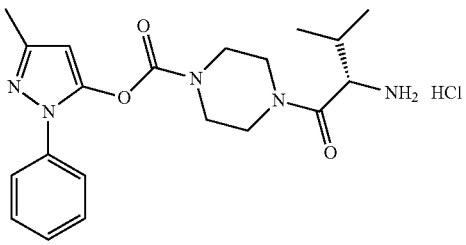 [SMILES: Cc1cc(OC(=O)N2CCN(C(=O)[C@@H](N)C(C)C)CC2)n(-c2ccccc2)n1 ; Cl]

Using 1.0 g of benzyl piperazine-1-carboxylate and 0.99 g of N-Boc-valine, 0.39 g (20.4%) of the title compound as an off-white solid was obtained according to the method of Synthesis Example 2. The results of nuclear magnetic resonance analysis and mass spectrometry are shown in Table 2 below.

Example 11: (R)-3-methyl-1-phenyl-1H-pyrazol-5-yl 4-((S)-2-amino-3-methylbutanoyl)-2-methylpiperazine-1-carboxylate Hydrochloride

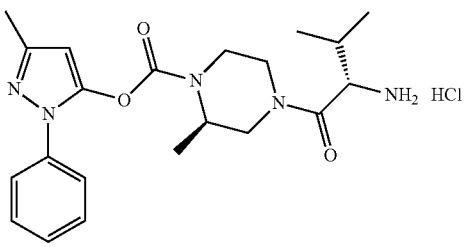 [SMILES: Cc1cc(OC(=O)N2CCN(C(=O)[C@@H](N)C(C)C)C[C@H]2C)n(-c2ccccc2)n1 ; Cl]

Using 1.0 g of (R)-benzyl 2-methylpiperazine-1-carboxylate and 0.93 g of N-Boc-valine, 0.35 g (18.8%) of the title compound as an off-white solid was obtained according to the method of Synthesis Example 2. The results of nuclear magnetic resonance analysis and mass spectrometry are shown in Table 2 below.

Example 12: (S)-3-methyl-1-phenyl-1H-pyrazol-5-yl 4-((S)-2-amino-3-methylbutanoyl)-2-methylpiperazine-1-carboxylate Hydrochloride

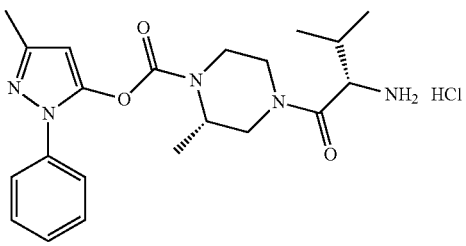 [SMILES: Cc1cc(OC(=O)N2CCN(C(=O)[C@@H](N)C(C)C)C[C@@H]2C)n(-c2ccccc2)n1 ; Cl]

Using 1.0 g of (S)-benzyl 2-methylpiperazine-1-carboxylate and 0.93 g of N-Boc-valine, 0.30 g (16.1%) of the title compound as an off-white solid was obtained according to the method of Synthesis Example 2. The results of nuclear magnetic resonance analysis and mass spectrometry are shown in Table 2 below.

Example 13: (R)-3-methyl-1-phenyl-1H-pyrazol-5-yl 4-((S)-2-amino-3-methylbutanoyl)-2-ethylpiperazin-1-carboxylate Hydrochloride

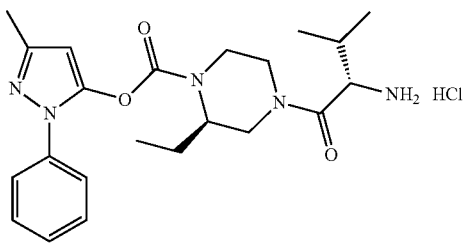 [SMILES: CC[C@@H]1CN(C(=O)[C@@H](N)C(C)C)CCN1C(=O)Oc1cc(C)nn1-c1ccccc1 ; Cl]

Using 1.0 g of (R)-benzyl 2-ethylpiperazine-1-carboxylate and 0.87 g of N-Boc-valine, 0.15 g (8.3%) of the title compound as an off-white solid was obtained according to the method of Synthesis Example 2. The results of nuclear magnetic resonance analysis and mass spectrometry are shown in Table 2 below.

Example 14: (S)-3-methyl-1-phenyl-1H-pyrazol-5-yl 4-((S)-2-amino-3-methylbutanoyl)-3-methylpiperazin-1-carboxylate Hydrochloride

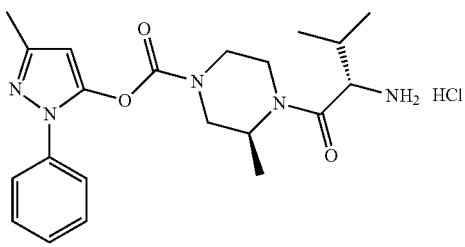 [SMILES: Cc1cc(OC(=O)N2CCN(C(=O)[C@@H](N)C(C)C)[C@@H](C)C2)n(-c2ccccc2)n1 ; Cl]

Using 1.0 g of (S)-benzyl 3-methylpiperazine-1-carboxylate and 0.93 g of N-Boc-valine, 0.36 g (19.3%) of the title compound as an off-white solid was obtained according to the method of Synthesis Example 2. The results of nuclear magnetic resonance analysis and mass spectrometry are shown in Table 2 below.

Example 15: (S)-3-methyl-1-phenyl-1H-pyrazol-5-yl 4-(2-amino-3,3-dimethylbutanoyl)piperazine-1-carboxylate Hydrochloride

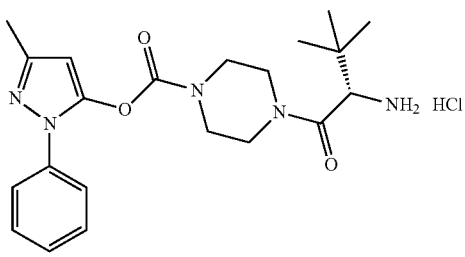 [SMILES: Cc1cc(OC(=O)N2CCN(C(=O)[C@@H](N)C(C)(C)C)CC2)n(-c2ccccc2)n1 ; Cl]

Using 1.0 g of benzyl piperazine-1-carboxylate and 1.05 g of N-Boc-t-leucine, 0.38 g (19.2%) of the title compound as an off-white solid was obtained according to the method of Synthesis Example 2. The results of nuclear magnetic resonance analysis and mass spectrometry are shown in Table 2 below.

Example 16: (S)-3-methyl-1-phenyl-1H-pyrazol-5-yl 4-(2-amino-4-(methylthio)butanoyl)piperazine-1-carboxylate Hydrochloride

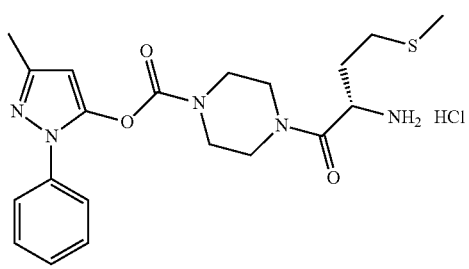

Using 1.0 g of benzyl piperazine-1-carboxylate and 1.13 g of N-Boc-methionine, 0.28 g (13.6%) of the title compound as an off-white solid was obtained according to the method of Synthesis Example 2. The results of nuclear magnetic resonance analysis and mass spectrometry are shown in Table 2 below.

Example 17: (S)-3-methyl-1-phenyl-1H-pyrazol-5-yl 4-(2-amino-3-phenylpropanoyl)piperazine-1-carboxylate Hydrochloride

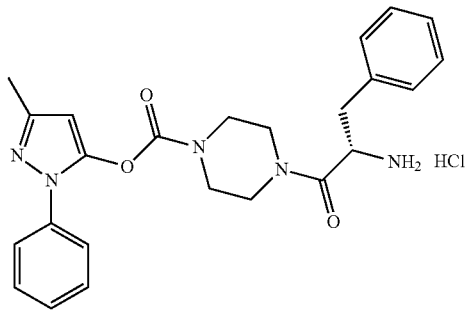 [SMILES: Cc1cc(OC(=O)N2CCN(C(=O)[C@@H](N)Cc3ccccc3)CC2)n(-c2ccccc2)n1 ; Cl]

Using 1.0 g of benzyl piperazine-1-carboxylate and 1.20 g of N-Boc-phenylalanine, 0.35 g (16.4%) of the title compound as an off-white solid was obtained according to the method of Synthesis Example 2. The results of nuclear magnetic resonance analysis and mass spectrometry are shown in Table 2 below.

Example 18: (S)-3-methyl-1-phenyl-1H-pyrazol-5-yl 4-(2,4-diamino-4-oxobutanoyl)piperazine-1-carboxylate Hydrochloride

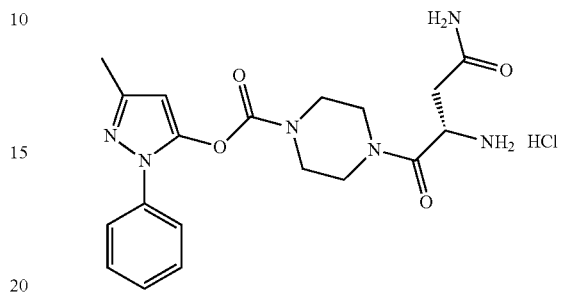

Using 1.0 g of benzyl piperazine-1-carboxylate and 1.05 g of N-Boc-asparagine, 0.15 g (7.6%) of the title compound as a brown solid was obtained according to the method of Synthesis Example 2. The results of nuclear magnetic resonance analysis and mass spectrometry are shown in Table 2 below.

Example 19: (S)-3-methyl-1-phenyl-1H-pyrazol-5-yl 4-(2,6-diaminohexanoyl)piperazine-1-carboxylate Dihydrochloride

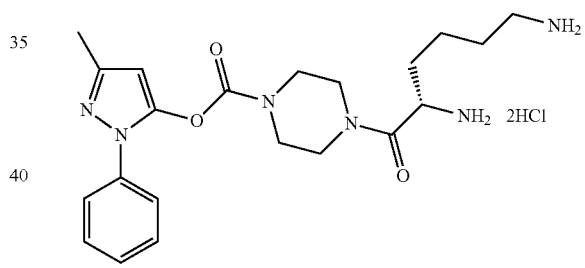

Using 1.0 g of benzyl piperazine-1-carboxylate and 1.57 g of N,N'-di-Boc-lysine, 0.20 g (9.0%) of the title compound as a brown solid was obtained according to the method of Synthesis Example 2. The results of nuclear magnetic resonance analysis and mass spectrometry are shown in Table 2 below.

The results of nuclear magnetic resonance analysis and mass spectrometry of the above examples are shown in Table 2 below.

TABLE 2

| Compound | Nuclear Magnetic Resonance Analysis | Mass Analysis |
|---|---|---|
| Example 1 | $^1$H NMR (400 MHz, DMSO-$d_6$) δ 2.18 (3H, s), 2.32 (3H, s), 3.35-3.65 (8H, m), 6.10 (1H, s), 7.45-7.66 (5H, m) | $[M + 1]^+$, 329.0 |
| Example 2 | $^1$H NMR (400 MHz, DMSO-$d_6$) δ 1.30 (3H, d), 2.17 (3H, s), 2.30 (3H, s), 3.28-3.55 (6H, m), 4.32 (1H, q), 6.07 (1H, s), 7.40-7.58 (5H, m) | $[M + 1]^+$, 343.0 |
| Example 3 | $^1$H NMR (400 MHz, DMSO-$d_6$) δ 1.30 (3H, d), 2.17 (3H, s), 2.30 (3H, s), 3.28-3.55 (6H, m), 4.32 (1H, q), 6.07 (1H, s), 7.40-7.58 (5H, m) | $[M + 1]^+$, 343.0 |
| Example 4 | $^1$H NMR (400 MHz, DMSO-$d_6$) δ 1.32-1.60 (10H, m), 2.20 (3H, s), 2.32-2.35 (1H, m), 3.38-3.95 (8H, m), 6.09 (1H, s), 7.32-7.50 (5H, m) | $[M + 1]^+$, 397.1 |

TABLE 2-continued

| Compound | Nuclear Magnetic Resonance Analysis | Mass Analysis |
|---|---|---|
| Example 5 | $^1$H NMR (400 MHz, DMSO-$d_6$) δ 2.18 (3H, s), 3.35-3.65 (8H, m), 6.10 (1H, s), 7.40-7.69 (10H, m) | $[M + 1]^+$, 391.0 |
| Example 6 | $^1$H NMR (400 MHz, DMSO-$d_6$) δ 2.20 (3H, s), 3.30-3.60 (8H, m), 3.80-3.82 (2H, m), 6.08 (1H, s), 7.31-7.46 (5H, m), 8.35 (3H, br s) | $[M + 1]^+$, 344.0 |
| Example 7 | $^1$H NMR (400 MHz, DMSO-$d_6$) δ 1.16 (3H, d), 2.17 (3H, s), 3.30-3.60 (8H, m), 3.74 (1H, q), 6.05 (1H, s), 7.35-7.49 (5H, m), 8.25 (3H, br s) | $[M + 1]^+$, 358.0 |
| Example 8 | $^1$H NMR (400 MHz, DMSO-$d_6$) δ 2.16 (3H, s), 3.32-3.58 (8H, m), 3.65-3.68 (1H, m), 3.82-4.02 (2H, m), 6.07 (1H, s), 7.28-7.50 (5H, m), 8.22 (3H, br s) | $[M + 1]^+$, 374.0 |
| Example 9 | $^1$H NMR (400 MHz, DMSO-$d_6$) δ 2.15 (3H, s), 2.94-3.19 (2H, m), 3.30-3.59 (8H, m), 3.78-3.88 (1H, t), 6.07 (1H, s), 7.29-7.50 (5H, m), 8.21 (3H, br s) | $[M + 1]^+$, 390.1 |
| Example 10 | $^1$H NMR (400 MHz, DMSO-$d_6$) δ 0.94 (6H, d), 1.95-2.05 (1H, m), 2.17 (3H, s), 3.30-3.65 (8H, m), 4.22 (1H, d), 6.07 (1H, s), 7.30-7.49 (5H, m), 8.14 (3H, br s) | $[M + 1]^+$, 386.1 |
| Example 11 | $^1$H NMR (400 MHz, DMSO-$d_6$) δ 0.91 (6H, d), 1.33 (3H, d), 1.96-2.01 (1H, m), 2.18 (3H, s), 3.30-3.61 (6H, m), 4.20 (1H, d), 4.35-4.38 (1H, m), 6.06 (1H, s), 7.28-7.52 (5H, m), 8.56 (3H, br s) | $[M + 1]^+$, 400.1 |
| Example 12 | $^1$H NMR (400 MHz, DMSO-$d_6$) δ 0.92 (6H, d), 1.35 (3H, d), 1.96-2.00 (1H, m), 2.15 (3H, s), 3.28-3.60 (6H, m), 4.21 (1H, d), 4.36-4.38 (1H, m), 6.07 (1H, s), 7.28-7.52 (5H, m), 8.44 (3H, br s) | $[M + 1]^+$, 400.1 |
| Example 13 | $^1$H NMR (400 MHz, DMSO-$d_6$) δ 0.90 (6H, d), 0.95 (3H, t), 1.64-1.68 (2H, m), 1.98-2.00 (1H, m), 2.16 (3H, s), 3.28-3.60 (6H m), 4.19 (1H, d), 4.40-4.43 (1H, m), 6.07 (1H, s), 7.30-7.52 (5H, m), 8.21 (3H, br s) | $[M + 1]^+$, 414.1 |
| Example 14 | $^1$H NMR (400 MHz, DMSO-$d_6$) δ 0.90 (6H, d), 1.31 (3H, d), 1.97-2.01 (1H, m), 2.18 (3H, s), 3.32-3.60 (6H, m), 4.22 (1H, d), 4.38-4.45 (1H, m), 6.07 (1H, s), 7.31-7.58 (5H, m), 8.46 (3H, br s) | $[M + 1]^+$, 400.1 |
| Example 15 | $^1$H NMR (400 MHz, DMSO-$d_6$) δ 0.95 (9H, s), 2.18 (3H, s), 3.30-3.60 (8H, m), 4.20 (1H, s), 6.08 (1H, s), 7.31-7.51 (5H, m), 8.14 (3H, br s) | $[M + 1]^+$, 400.1 |
| Example 16 | $^1$H NMR (400 MHz, DMSO-$d_6$) δ 2.04-2.08 (2H, m), 2.15 (3H, s), 2.20 (3H, s), 2.57 (2H, t), 3.28-3.66 (9H, m), 6.06 (1H, s), 7.29-7.52 (5H, m), 8.80 (3H, br s) | $[M + 1]^+$, 418.1 |
| Example 17 | $^1$H NMR (400 MHz, DMSO-$d_6$) δ 2.17 (3H, s), 3.15-3.68 (10H, m), 3.97-4.02 (1H, m), 6.10 (1H, s), 7.31-7.62 (10H, m), 8.36 (3H, br s) | $[M + 1]^+$, 434.1 |
| Example 18 | $^1$H NMR (400 MHz, DMSO-$d_6$) δ 2.15 (3H, s), 2.56-2.65 (2H, m), 3.33-3.55 (8H, m), 3.89-3.92 (1H, m), 6.10 (1H, s), 6.66 (2H, br s), 7.31-7.55 (5H, m), 8.47 (3H, br s) | $[M + 1]^+$, 401.1 |
| Example 19 | $^1$H NMR (400 MHz, DMSO-$d_6$) δ 1.22-1.25 (2H, m), 1.58-1.62 (2H, m), 1.79-1.84 (2H, m), 2.15 (3H, s), 2.78-2.82 (2H, m), 3.30-3.62 (9H, m), 5.67 (3H, br s), 6.07 (1H, s), 7.31-7.50 (5H, m), 8.81 (3H, br s) | $[M + 1]^+$, 415.1 |

Experimental Example 1: Pharmacokinetic Evaluation

The pharmacokinetic test of the compounds of Examples and Reference Example was carried out as follows. That is, after a single oral administration of the test compound to SD (Sprague-Dawley) rats, the efficacy of the compound of the present invention was verified by tracking the kinetics of the edaravone released into the blood by metabolic processes and comparing it with a standard substance. Specifically, edaravone, a standard substance, was administered intravenously and orally, respectively, and the test compounds were administered orally. Then, the concentration of edaravone in blood was evaluated. The standard substance and the test compounds were each prepared in the same manner and then administered to rats at a dose of 0.1 mmol/kg, and blood was collected at a predetermined time and plasma was separated. Analysis of the drug was performed using HPLC (XBridge column Cis, Waters, mobile phase 0.1% formic acid:acetonitrile (30:70, %/%)) and MS/MS (ESI positive, MRM). Each commercial standard solution was mixed in a ratio of 9:1 with rat plasma to prepare and calibrate at concentrations of 5, 50, 100, 500, 1000 and 5000 ng/ml. In addition, the QC sample was prepared by mixing the rat plasma and the standard solution for QC at a ratio of 9:1, and at concentrations of 100, 750 and 2,500 ng/ml. In the pretreatment method, 100 μl of plasma sample was transferred to a tube for centrifugation, 10 μl of an internal standard solution and 300 μl of methanol were added, followed by mixing for about 30 seconds. The tube was centrifuged at 3,000×g (4° C.) for about 5 minutes, the supernatant was taken and transferred to an LC vial, and then injected into the instrument. In addition, the concentration of an active ingredient, that is, edaravone, in rat plasma was quantified by applying a previously validated analysis method. For pharmacokinetic parameters, WinNonlin 5.2 (Pharsight, USA) program was used, and $AUC_{0-t}$, $AUC_{0-\infty}$, $C_{max}$, $T_{max}$, and $t_{1/2}$ were calculated by noncompartment modeling (best fit). The pharmacokinetic parameter results were expressed as mean and standard deviation (SD), and statistically processed using the SPSS program (Statistical Package for the Social Sciences, 10.0K, USA).

After the test, each bioavailability after oral administration of standard substance and test compounds is summarized in Table 3 below.

TABLE 3

| Test Compound | Bioavailability (F, %) |
|---|---|
| Standard substance (edaravone) | 4.9 |

TABLE 3-continued

| Test Compound | Bioavailability (F, %) |
| --- | --- |
| Example 1 | 23.0 |
| Example 2 | 20.5 |
| Example 3 | 19.2 |
| Example 4 | 29.6 |
| Example 5 | 32.3 |
| Example 6 | 54.9 |
| Example 7 | 56.5 |
| Example 8 | 49.1 |
| Example 9 | 48.8 |
| Example 10 | 88.2 |
| Example 11 | 59.8 |
| Example 12 | 57.2 |
| Example 13 | 46.9 |
| Example 14 | 64.5 |
| Example 15 | 60.7 |
| Example 16 | 41.1 |
| Example 17 | 56.6 |
| Example 18 | 57.0 |
| Example 19 | 71.2 |
| Reference Example 1 | 12.0 |

For the representative Example 10 compound, the average $AUC_t$ is 9,835 hr*ng/ml, the average $AUC_i$ is 9,856 hr*ng/ml, the average $C_{max}$ is 1,803 ng/ml, the average $T_{max}$ is 1.00 hour, the average $t_{1/2}$ is 2.51 hours, and the bioavailability was 88.2%. On the other hand, for Example 15 compound, the average $AUC_t$ was 6,772 hr*ng/ml, the average $AUC_i$ was 6,795 hr*ng/ml, the average $C_{max}$ was 1,696 ng/ml, the average $T_{max}$ was 0.42 hours, and the average $t_{1/2}$ was 2.69 hours, and the bioavailability was 60.7%. After oral administration of Example 10 compound and Example 15 compound, the blood concentration of edaravone over time is as shown in FIGS. 1 and 2, respectively.

As shown in the results of Table 3, in particular, the oral bioavailability of the compounds of Example 10, Example 19, Example 14, and Example 15 was excellent.

The invention claimed is:

1. A compound represented by the following Chemical formula 1 or a pharmaceutically acceptable salt thereof:

[Chemical Formula 1]

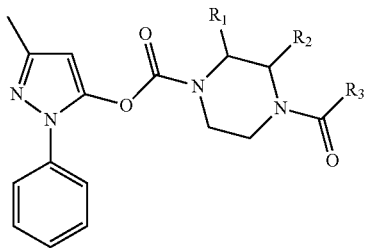

In Chemical Formula 1, $R_1$ and $R_2$ are each independently hydrogen or $(C_1$-$C_3)$ alkyl, $R_3$ is any one selected from the group consisting of $(C_1$-$C_3)$alkyl, $(C_3$-$C_7)$cycloalkyl, phenyl, —$CH_2NH_2$, —$CH(CH_3)NH_2$, —$CH(CH_2OH)NH_2$, —$CH(CH(CH_3)OH)NH_2$, —$CH(CH_2SH)NH_2$, —$CH(CH(CH_3)_2)NH_2$, —$CH(C(CH_3)_3)NH_2$, —$CH(CH_2CH(CH_3)_2)NH_2$, —$CH(CH(CH_3)CH_2CH_3)NH_2$, —$CH(CH_2CH_2SCH_3)NH_2$, pyrrolidin-2-yl, —$CH(CH_2Ph)NH_2$, —$CH(CH_2PhOH$-$p)NH_2$, —$CH(1H$-indole-3-yl-$CH_2)NH_2$, —$CH(CH_2CO_2H)NH_2$, —$CH(CH_2CH_2CO_2H)NH_2$, —$CH(CH_2CONH_2)NH_2$, —$CH(CH_2CH_2CONH_2)NH_2$, —$CH(1H$-imidazol-4-yl-$CH_2)NH_2$, —$CH_2CH_2CH_2CH_2NH_2$, and —$CH_2CH_2CH_2NHC(NH)NH_2$.

2. The compound or a pharmaceutically acceptable salt thereof according to claim 1, wherein the compound is 3-methyl-1-phenyl-1H-pyrazol-5-yl 4-acetylpiperazine-1-carboxylate;

(S)-3-methyl-1-phenyl-1H-pyrazol-5-yl 4-acetyl-2-methylpiperazine-1-carboxylate;

(R)-3-methyl-1-phenyl-1H-pyrazol-5-yl 4-acetyl-2-methylpiperazine-1-carboxylate;

3-methyl-1-phenyl-1H-pyrazol-5-yl 4-(cyclohexanecarbonyl)piperazine-1-carboxylate;

3-methyl-1-phenyl-1H-pyrazol-5-yl 4-benzoylpiperazine-1-carboxylate;

3-methyl-1-phenyl-1H-pyrazol-5-yl 4-(2-aminoacetyl) piperazine-1-carboxylate;

(S)-3-methyl-1-phenyl-1H-pyrazol-5-yl 4-(2-aminopropanoyl)piperazine-1-carboxylate;

(S)-3-methyl-1-phenyl-1H-pyrazol-5-yl 4-(2-amino-3-hydroxypropanoyl)piperazine-1-carboxylate;

(R)-3-methyl-1-phenyl-1H-pyrazol-5-yl 4-(2-amino-3-mercaptopropanoyl)piperazine-1-carboxylate;

(S)-3-methyl-1-phenyl-1H-pyrazol-5-yl 4-(2-amino-3-methylbutanoyl)piperazine-1-carboxylate;

(R)-3-methyl-1-phenyl-1H-pyrazol-5-yl 4-((S)-2-amino-3-methylbutanoyl)-2-methylpiperazine-1-carboxylate;

(S)-3-methyl-1-phenyl-1H-pyrazol-5-yl 4-((S)-2-amino-3-methylbutanoyl)-2-methylpiperazine-1-carboxylate;

(R)-3-methyl-1-phenyl-1H-pyrazol-5-yl 4-((S)-2-amino-3-methylbutanoyl)-2-ethylpiperazine-1-carboxylate;

(S)-3-methyl-1-phenyl-1H-pyrazol-5-yl 4-((S)-2-amino-3-methylbutanoyl)-3-methylpiperazine-1-carboxylate;

(S)-3-methyl-1-phenyl-1H-pyrazol-5-yl 4-(2-amino-3,3-dimethylbutanoyl)piperazine-1-carboxylate;

(S)-3-methyl-1-phenyl-1H-pyrazol-5-yl 4-(2-amino-4-(methylthio)butanoyl)piperazine-1-carboxylate;

(S)-3-methyl-1-phenyl-1H-pyrazol-5-yl 4-(2-amino-3-phenylpropanoyl)piperazine-1-carboxylate;

(S)-3-methyl-1-phenyl-1H-pyrazol-5-yl 4-(2,4-diamino-4-oxobutanoyl)piperazine-1-carboxylate;

or (S)-3-methyl-1-phenyl-1H-pyrazol-5-yl 4-(2,6-diaminohexanoyl)piperazine-1-carboxylate.

3. A pharmaceutical composition comprising the compound of claim 1 or a pharmaceutically acceptable salt thereof, and a pharmaceutically acceptable carrier.

4. A method for treating or alleviating Alzheimer's disease, Parkinson's disease, or Lou Gehrig's disease in a subject in need thereof, comprising administering to the subject a pharmaceutical composition comprising the compound of claim 1 or a pharmaceutically acceptable salt thereof as an active ingredient.

5. A pharmaceutical composition comprising the compound of claim 2 or a pharmaceutically acceptable salt thereof, and a pharmaceutically acceptable carrier.

6. A method for treating or alleviating Alzheimer's disease, Parkinson's disease, or Lou Gehrig's disease in a subject in need thereof, comprising administering to the subject a pharmaceutical composition comprising the compound of claim 2 or a pharmaceutically acceptable salt thereof as an active ingredient.

* * * * *